(12) United States Patent
Carli et al.

(10) Patent No.: US 9,468,602 B2
(45) Date of Patent: Oct. 18, 2016

(54) PHARMACEUTICAL MICROEMULSION FOR PREVENTING SUPRAMOLECULAR AGGREGATION OF AMPHIPHILIC MOLECULES

(75) Inventors: Fabio Carli, Trieste (IT); Elisabetta Chiellini, Trieste (IT); Van Van Khov-Tran, Pfäffikon (CH); Mihran Baronian, Toffen (CH)

(73) Assignee: AZAD Pharma AG, Toffen (CH)

( * ) Notice: Subject to any disclaimer, the term of this patent is extended or adjusted under 35 U.S.C. 154(b) by 1439 days.

(21) Appl. No.: 13/143,241

(22) PCT Filed: Jan. 5, 2010

(86) PCT No.: PCT/EP2010/050046
§ 371 (c)(1),
(2), (4) Date: Aug. 11, 2011

(87) PCT Pub. No.: WO2010/076340
PCT Pub. Date: Jul. 8, 2010

(65) Prior Publication Data
US 2011/0294746 A1 Dec. 1, 2011

(30) Foreign Application Priority Data
Jan. 5, 2009 (EP) .................... 09000055

(51) Int. Cl.
| | | |
|---|---|---|
| *A61K 9/10* | (2006.01) |
| *A61K 9/00* | (2006.01) |
| *A61K 9/107* | (2006.01) |
| *A61K 31/337* | (2006.01) |
| *A61K 47/10* | (2006.01) |
| *A61K 47/14* | (2006.01) |
| *A61K 47/26* | (2006.01) |
| *A61K 47/44* | (2006.01) |

(52) U.S. Cl.
CPC ........... *A61K 9/0019* (2013.01); *A61K 9/1075* (2013.01); *A61K 31/337* (2013.01); *A61K 47/10* (2013.01); *A61K 47/14* (2013.01); *A61K 47/26* (2013.01); *A61K 47/44* (2013.01)

(58) Field of Classification Search
CPC ............ A61K 9/0019; A61K 9/1075; A61K 31/337; A61K 47/10
USPC ....................................................... 424/450
See application file for complete search history.

(56) References Cited

U.S. PATENT DOCUMENTS

| | | | |
|---|---|---|---|
| 6,284,268 B1 * | 9/2001 | Mishra et al. ................ 424/455 |
| 6,979,456 B1 * | 12/2005 | Parikh et al. ................ 424/422 |
| 2003/0044434 A1 * | 3/2003 | Gao et al. .................... 424/400 |
| 2006/0067952 A1 | 3/2006 | Chen | |
| 2008/0175887 A1 | 7/2008 | Wang | |
| 2008/0255508 A1 | 10/2008 | Wang | |
| 2008/0276935 A1 | 11/2008 | Wang | |

FOREIGN PATENT DOCUMENTS

| | | |
|---|---|---|
| EP | 0 593 656 B1 | 1/1997 |
| EP | 0 645 145 B1 | 3/1997 |
| EP | 0 593 601 B1 | 12/1997 |
| EP | 1142568 A | 10/2001 |
| EP | 1067908 B9 | 5/2006 |
| GB | 2380673 A | 4/2003 |
| WO | 9320833 A | 10/1993 |
| WO | 94/07484 | 4/1994 |
| WO | 97/03651 | 2/1997 |
| WO | 97/30695 | 8/1997 |
| WO | 9906024 A | 2/1999 |
| WO | 99/22759 | 5/1999 |
| WO | 9929316 A | 6/1999 |
| WO | 9949848 A | 10/1999 |
| WO | 00/50007 A1 | 8/2000 |
| WO | 01/01960 A1 | 1/2001 |
| WO | 2004/009075 | 1/2004 |
| WO | 2007/103294 A2 | 9/2007 |
| WO | 2008/026048 A2 | 3/2008 |
| WO | 2008/063581 A2 | 5/2008 |

OTHER PUBLICATIONS

Tarr (Pharmaceutical Research 4(2) 162-165, 1987).*
Alberts et al.: "Safety Aspects of Pegylated Liposomal Doxorubicin in Patients with Cancer", Drugs, vol. 54, suppl. 4, 1997, pp. 30-35.
Cortes et al.: "Docetaxel", Journal of Clinical Oncology, vol. 13, No. 19, 1995, pp. 2643-2655.
Costa et al.: "Can we decrease amphoterici nephrotoxicity?", Current Opinion in Critical Care, vol. 7, No. 6, 2001, pp. 379-383.
Denman et al.: "Hypersensitivity Reaction (HSR) to Docetaxel After a Previous HSR to Paclitaxel", J Clin Oncol, vol. 20, 2002, pp. 2760-2761.
Essayan et al.: "Successful parenteral desensitization to paclitaxel", J Allergy Clin Immunol, vol. 97, No. 1, 1996, pp. 12-46.
Gaboriau et al: "Heat-Induced Superaggregation of Amphotericin B Reduces Its In Vitro Toxicity: a New Way to Improve Its Therapeutic Index", Antimicrobial Agents and Chemotherapy, vol. 41, No. 11, 1997, pp. 2345-2351.
Gelmon: "The taxoids: paclitaxel and docetaxel", Lancet, vol. 344, 1994, pp. 1267.
Lavasanifar et al.: "Block copolymer Micelles for the Encapsulation and Delivery of Amphotericin B", Pharmaceutical Research, vol. 19, No. 4, 2002, pp. 418-422.
Mertens et al.: "Docetaxel in advanced renal carcinoma; A phase II trial of the National Cancer Institute of Canada clinical Trials Group", Ann Oncol, vol. 5, No. 2, 1994, pp. 185-187.
Sanchez-Brunete et al.: "Amphoteri-cin B Molecular Organization as an Essential Factor to Improve Activity/Toxicity Ration in the Treatment of Visceral Leishmaniasis", vol. 12, No. 7, 2004, pp. 453-460.
Sharma et al.: "Antitumor Effect of Taxol-containing Liposomes in a Taxol-resistant Murine Tumor Model", Cancer Research, vol. 53., 1993, pp. 5877-5881.
Sharma et al.: "Antitumor efficacy of taxane liposomes on a human ovarian tumor xenograft in nude athymic mice", J. Pharm. Sci., vol. 84, No. 12, 1995, pp. 1400-1404.

(Continued)

*Primary Examiner* — David Lukton
(74) *Attorney, Agent, or Firm* — Rothwell, Figg, Ernst & Manbeck, P.C.

(57) ABSTRACT

The present invention refers to a microemulsion formulation suitable for preventing assembly of amphiphilic drug molecules which may cause hypersensitivity reactions and other unwanted side effects.

18 Claims, 9 Drawing Sheets

(56) References Cited

OTHER PUBLICATIONS

Szebeni: "The Interaction of Liposomes with the Complement System", Crit Rev Ther Drug Carrier Syst, vol. 15, No. 1, 1998.
Szebeni et al.: "Formation of complement-activating particles in aqueous solutions of Taxol: possible role in hypersensitivity reactions", International Immuno-pharmacology, vol. 1, No. 4, 2001, pp. 721-735.
Wong-Beringer et al.: "Lipid Formulations of Amphotericin B: Clinical Efficacy and Toxicities", Clin Infect Dis, vol. 27, 1998, pp. 603-618.
Search Report for the corresponding European application No. 13160375.5-1460, dated Apr. 26, 2013, 6 pgs.

* cited by examiner

PHARMACEUTICAL MICROEMULSION FOR PREVENTING SUPRAMOLECULAR AGGREGATION OF AMPHIPHILIC MOLECULES

CROSS REFERENCE TO RELATED APPLICATION

This application is a 35 U.S.C. 371 National Phase Entry Application from PCT/EP2010/050046, filed Jan. 5, 2010, which claims the benefit of European Patent Application No. 09000055.5 filed on Jan. 5, 2009, the disclosure of which is incorporated herein in its entirety by reference.

The present invention refers to a microemulsion formulation suitable for preventing superaggregation of amphiphilic substances which aggregates may cause hypersensitivity reactions and other unwanted side effects.

Presently, there are injectables on the market comprising hardly soluble drugs, such as taxol, docetaxel, amphotericin B, and doxorubicin which in some clinical cases caused high-sensitivity reactions (HSR), unwanted side-effects such as flushing, chest pain, tachycardia, hypotension, and sometimes death of the patient. Such strong side-effects could be reduced by administering the infusions over longer periods of times and by pre-treating the patients with steroids, antihistamines and H2-antagonists (1-2). In all these cases, the HSR effects have been attributed both to the drug per se and to the excipients/delivery systems such as surfactants, liposomes, etc. (3-9).

However, toxicity of the drugs can originate not only from biochemical intracellular adverse interactions or systemic allergic reactions linked to the specific chemical structure of the drug molecule, but also from its molecular aggregation state.

For example, though some contradictory interpretations still exist, there is growing evidence that aggregates of the antifungal drug amphotericin B may result in intravenously infusion-related hypersensitivity side-effects and in drug precipitation causing obstruction of renal tubules (10). Also haemolytic activity of amphotericin B has been shown to depend on the formation of molecular aggregates (11).

On the other hand, modification of amphotericin B molecular aggregation state resulted in reduction of toxicity (12) and was found to be the key factor determining drug activity/toxicity ratio (13).

Paclitaxel is a drug which is hardly soluble in both polar solvents and non-polar solvents. Also in this case, the marketed formulations are reported to cause hypersensitivity reactions which have been attributed both to the drug and to the non-ionic emulsifier vehicle.

The dilution of the commercial injection concentrates into infusion solution results in micelle-like molecular aggregates and needle-like structures which cause the activation of the immunogenic system which consequently induce hypersensitivity reactions (14).

Docetaxel is another taxane drug, which has been found to cause acute HSR (15-16). Substitution of paclitaxel with docetaxel does not eliminate HSR (17), rebutting the possible attribution to the taxane moiety of the etiologic factor in the hypersensitivity side-effects. Also for docetaxel the potential molecular aggregation tendency can be the basis for HSR (18).

Not only amphiphilic drugs can self-assemble and thus lead to hypersensitivity reactions due to molecular aggregates but also amphiphilic excipients can undergo the same supramolecular aggregation phenomenon causing severe side-effects. Excipients such as surfactants having long hydrophobic chains with strongly polar head groups form micelles above the critical micelle concentration (CMC), i.e. large supramolecular aggregates potentially stimulating immunogenic reactions.

There are several pharmaceutical compositions known in the prior art for solubilising drug components via emulsion formulations, however therein superaggregation can not be excluded.

WO 00/50007 discloses a pharmaceutical composition comprising a hydrophobic therapeutic agent and a carrier, wherein the carrier comprises at least one hydrophilic surfactant and at least one hydrophobic surfactant which are present in an amount that upon mixing with an aqueous solution a clear aqueous dispersion is obtained. Thus, in this system the surfactants are used to disperse the solid drug agglomerates in the aqueous phase.

WO 01/01960 discloses a pharmaceutical composition comprising a triglyceride, a carrier comprising at least two surfactants and a therapeutic agent which is capable of being solubilised in the triglyceride, in the carrier, or in both the triglyceride and the carrier. The triglyceride and the surfactants are present in an amount such that upon mixing with an aqueous solution the composition forms a clear aqueous dispersion. As mentioned above, the presence of a dispersion points to the fact that the therapeutic agent is present as a solid substance, i.e. in aggregates, and, thus, is not solved molecularly in the triglyceride or water phase of the emulsion.

EP 1 067 908 describes a self-emulsifying preconcentrate of a taxane in a microemulsion, consisting of 10-80 wt.-% of a hydrophobic component and 20-80 wt.-% of a surfactant comprising at least one non-ionic surfactant and further optional components, wherein the preconcentrate when mixed with an aqueous medium gives a microemulsion. Superaggregation of the pharmaceutically active agent has not been investigated.

US 2006/067952 describes an intravenously injectable oil-in-water-emulsion comprising a taxoid drug, an oil component, an ionic phospholipid component, and water.

Actually, a potentially HSR-preventing method for formulations containing amphiphilic vehicles has been recently proposed based on the use of specific complement C inhibitor substances, such as polyanions, diamines, synthetic peptides, antibodies, etc (19).

Also, WO 2004/009075 discloses a paclitaxel delivery system, wherein paclitaxel is solubilized. It is stated that this system does not form aggregates even after being dispersed in water. The formulation is composed of at least one monoglyceride compound, at least one oil, and paclitaxel.

However, there is still a need for improved formulations with HSR-preventing properties wherein supra-molecularly aggregation of both amphiphilic drugs and excipients is minimized or inhibited.

Surprisingly, it has now been found that a microemulsion comprising at least one amphiphilic substance, at least one oily component, an aqueous phase, at least two structurally different non-ionic surfactants, at least one polarity modifier and at least one cosurfactant is suitable for injectables without any self-assembled aggregates being formed.

Thus, one aspect of the present invention is directed to a microemulsion, comprising
 (i) at least one amphiphilic substance,
 (ii) at least one oily component,
 (iii) an aqueous phase,
 (iv) at least two structurally different non-ionic surfactants, (v) at least one polarity modifier and
(vi) at least one cosurfactant.

The term "amphiphilic substance" refers to a compound exhibiting a polar and a non-polar domain.

The amphiphilic substance is preferably substantially insoluble in water and preferably has a solubility in water of lower than 5 g/l, more preferably of lower than 2 g/l, and even more preferably of lower than 0.5 g/l at room temperature.

In another embodiment, the amphiphilic substance has also a low solubility in non-polar solvents. The solubility of the amphiphilic substance in benzene is preferably lower than 0.5 g/l at room temperature.

In one embodiment, the amphiphilic substance is an amphiphilic pharmaceutically active agent or an amphiphilic drug, in particular an amphiphilic drug.

In a preferred embodiment, the pharmaceutically active agent may have anti-tumoral, antibiotic immunosuppressant, antibacterial, antifungal, ACE inhibiting, anti-asthma, anti-depressant, antipsychotic, respiratory stimulating, anti-pulmonary hypertension and anti-diabetic properties, but is not limited thereto.

Examples of pharmaceutically active agents are drugs such as taxanes and taxane derivatives, e.g. paclitaxel, docetaxel, etoposide, vinblastine, doxorubicine, epirubicine, idarubicine; platinum compounds, e.g. cisplatin, carboplatin, oxaliplatin; cyclosporine, ansamycin, erythromycin, tetracycline, amphotericin B, enalapril, salbutamol, zometapine and droperidol, however, are not limited thereto.

In a preferred embodiment, the pharmaceutically active agent is selected from the group consisting of taxanes and taxane derivatives, such as paclitaxel, docetaxel, etoposide, vinblastine, doxorubicine, epirubicine, idarubicine, and platinum compounds, such as cisplatin, carboplatin, oxaliplatin.

In an even more preferred embodiment, the pharmaceutically active agent is a taxane or a taxane derivative, e.g. paclitaxel, docetaxel, etoposide, vinblastine, doxorubicine, epirubicine, idarubicine.

The term "derivative" as used herein means a compound having a basic structure, e.g. a taxane structure, to which suitable substituents are bound via covalent bonds and/or physical interactions.

In another embodiment the amphiphilic substance is an excipient e.g. a molecule having both hydrophobic and hydrophilic domains.

Examples of excipients are surfactants such as polyoxyalkylene alkyl ethers, polyoxyalkylene sorbitane fatty acid esters, polyglycerol fatty acid esters, sodium lauryl sulphate, but are not limited thereto.

In a preferred embodiment, the microemulsion according to the invention contains a single amphiphilic substance, preferably a single pharmaceutically active agent, more preferably a single drug.

In another embodiment of the present invention, the microemulsion contains two different amphiphilic substances, preferably two different pharmaceutically active agents, more preferably two different drugs.

According to the invention, the microemulsion preferably comprises the amphiphilic substance (component (i)) in an amount of 0.0001 to 5.0 wt.-%, more preferably of 0.001 to 3 wt.-%, even more preferably of 0.001-1 wt.-% based on the total weight of the microemulsion.

The oily component (ii) is insoluble in water. As used herein, the term "insoluble in water" means a solubility in water of less than 2.0 g/l, preferably less than 0.5 g/l, more preferably 0.2 g/l.

In a preferred embodiment, the oily component is a fatty acid ester or/and a fatty acid.

In a more preferred embodiment, the oily component is selected from the group consisting of
- fatty acid triglycerides, such as glyceryl tricaprate, glyceryl trilaurate, glyceryl trilinoleate, natural occurring oils deriving from plants or animals such as olive oil, sesame oil, sunflower oil, soybean oil, castor oil and fish oil, but not limited thereto.
- fatty acid diglycerides, such as propylene glycol caprylate, propylene glycol caprate, diolein, dilinoleate, but not limited thereto.
- fatty acid monoglycerides such as monoolein, monopalmitolein, monomyristolein, but not limited thereto.
- fatty acid esters of monohydric alcohol such as ethyl oleate, isopropyl myristate, isopropyl palmitate, but not limited thereto.
- fatty acids such as oleic acid, linoleic acid, fish oil, but not limited thereto.

and mixtures thereof.

"Fatty acid" as used herein means a straight or branched chain, saturated or unsaturated, optionally substituted, hydrocarbon with at least 8, preferably at least 10, preferably at least 12, more preferably at least 14, even more preferably at least 16 and most preferably at least 20 carbon atoms having a carboxylic acid functional group.

In a preferred embodiment, "monohydric alcohol" is a $C_{1-8}$ monohydric alcohol, preferably a $C_{1-5}$ monohydric alcohol, such as for example methanol, ethanol, propanol or isopropanol.

In particular, monohydric alcohol is methanol, ethanol, propanol or isopropanol, even more preferably methanol, ethanol and isopropanol, and most preferably ethanol and isopropanol.

As used herein the term "fatty acid (mono-, di- or tri-) glycerides" refers to compounds wherein one, two or three hydroxy groups of glycerol are esterified or/and etherified with optionally hydrogenated synthetic or naturally occurring fatty acid(s) whereas possibly remaining hydroxy groups of the glycerol (if any) rest unreacted.

In another embodiment, the oily component is selected from the group consisting of fatty acid triglycerides, fatty acids, fatty acid esters of monohydric alcohols and mixtures thereof.

In another embodiment, the oily component is selected from the group consisting of fatty acid mono-, di-, triglycerides, fatty acid esters of monohydric alcohols and mixtures thereof.

In another embodiment, the oily component is selected from the group consisting of fatty acids, fatty acid mono-, diglycerides, fatty acid esters of monohydric alcohols and mixtures thereof.

In another embodiment, the oily component is selected from the group consisting of fatty acids, fatty acid triglycerides, fatty acid esters of monohydric alcohols and mixtures thereof.

In another embodiment, the oily component is selected from the group consisting of fatty acid mono-, di-, triglycerides and mixtures thereof.

In another embodiment, the oily component is selected from the group consisting of fatty acids, fatty acid mono-, diglycerides and mixtures thereof.

In another embodiment, the oily component is selected from the group consisting of fatty acid esters of monohydric alcohol, fatty acid triglycerides and mixtures thereof.

In another embodiment, the oily component is selected from the group consisting of fatty acid mono-, diglycerides, fatty acid esters of monohydric alcohols and mixtures thereof.

In another embodiment, the oily component is selected from the group consisting of fatty acids, fatty acid triglycerides and mixtures thereof.

In another embodiment, the oily component is selected from the group consisting of fatty acids, fatty acid esters of monohydric alcohols and mixtures thereof.

In another embodiment, the oily component is at least one fatty acid ester of a monohydric alcohol.

In a preferred embodiment the oily component is free of fatty acid triglycerides or/and fatty acid diglycerides or/and fatty acid monoglycerides.

In a preferred embodiment, the oily component is free of fatty acid mono- or diglycerides.

In another preferred embodiment, the oily component is free of fatty acid triglycerides.

In a preferred embodiment, the oily component contains one, two, three or four different oily compounds, in particular one or two, preferably one oily compound.

The oily component (component (ii)) is preferably present in an amount of 0.1-25 wt.-%, more preferably of 1-25 wt.-%, and even more preferably of 1-20 wt.-% based on the total weight of the microemulsion.

The aqueous phase (component (iii)) according to the invention comprises water, preferably a pharmaceutically acceptable type of water, such as sterile water, deionized water, or water for injectables according to Eur. Pharmc.

The aqueous phase may further comprise a water soluble formulation aid known in the art which are e.g. suitable for adjusting pH value, viscosity, taste, stability etc. Examples for formulation aids are buffers such as calcium citrate, citric acid, potassium phosphate, sodium borate, sodium gluconate, isotonic agents such as sucrose, sodium chloride, potassium chloride, sorbitol, mannitol, viscosity-increasing polymers such as hyaluronate sodium, cellulose derivatives, polyvinylpyrrolidone, alginate sodium and chitosan, polyacrylic acid salts, and flavours such as vanillin, orange, but are not limited thereto.

The aqueous phase may be preferably present in an amount of 40-95 wt.-%, more preferably of 50-95 wt.-%, and even more preferably of 60-85 wt.-% based on the total weight of the microemulsion.

The formulation aid may be present in an amount of from 0 to 30 wt.-%, more preferably from 0 to 20 wt.-%, and even more preferably from 0 to 15 wt.-% based on the total amount of the aqueous phase.

An essential object of the present invention is that the microemulsion comprises at least two structurally different non-ionic surfactants (component (iv)) which are different from the oily component (ii). By combining two structurally different non-ionic surfactants, on the one hand the interaction between the oily component (ii) and the aqueous phase (iii) leads to a fine dispersion of the oil in the water phase and on the other hand the interaction between the oily component (ii) and the amphiphilic substance (i) can be individually adjusted to each system, so preventing the amphiphilic substance or/and amphiphilic excipient to aggregate.

"Non-ionic surfactants" as used herein are surfactants which do not exhibit an ionic charge under conditions under which they are used.

Examples of non-ionic surfactants are alkylglucosides, polyoxyalkylene alkyl ethers, polyoxyalkylene alkyl phenols, polyoxyalkylene fatty acid esters, polyoxyalkylene glycerol fatty acid esters, polyoxyalkylene sorbitane fatty acid esters, polyoxyalkylene block-copolymers, polyglycerol fatty acid esters, polyoxyalkylene glycerides, polyoxyalkylene sterols, polyoxyalkylene vegetable oils, polyoxyalkylene hydrogenated vegetable oils, polyglycerol ether, polyoxyalkylene glycerol ester, polyoxyalkylene, and polyvinylalcohol, but are not limited thereto.

In a preferred embodiment, at least two non-ionic surfactants may be selected from the group consisting of polyoxyethylene alkyl ethers, polyoxyethylene sorbitane fatty acid esters, polyoxyethylene fatty acid esters, polyoxyethylene glycerol fatty acid esters, polyoxyethylene polyoxypropylene block copolymers, polyglycerol fatty acid esters, polyoxyethylene sterols, polyoxyethylene, but are not limited thereto.

Because of the low water solubility of the amphiphilic substance, the amphiphilic substance is generally included in the oily component. As mentioned above, the amphiphilic substance which diffuses from the oily phase to the water phase often tends to form supramolecular aggregation.

In order to reduce the diffusion of the amphiphilic substance, it is advantageous that at least one of the at least two non-ionic surfactants is sterically voluminous and thus prevents the amphiphilic substance from migrating into the aqueous phase. In another preferred embodiment, the microemulsion contains at least two non-ionic surfactants being sterically voluminous. Examples for such voluminous non-ionic surfactants are polyoxyethylene-polyoxypropylene block copolymers, polyvinylalcohol, polyoxyethylene sorbitane fatty acid esters, polyoxyethylene alkyl ethers, and polyoxyethylene fatty acid esters, in particular polyoxyethylene-polyoxypropylene block copolymers, polyoxyethylene alkyl ethers, polyoxyethylene fatty acid esters, and polyoxyethylene sorbitane fatty acid esters, more preferably polyoxyethylene sorbitane fatty acid esters.

In a preferred embodiment, component (iv) is free of fatty acid monoglycerides or/and fatty acid diglycerides as defined above.

In a preferred embodiment, the microemulsion comprises 2, 3 or 4, preferably two non-ionic surfactants.

The total amount of the at least two non-ionic surfactants (component (iv)) is preferably in the range of 0.1-25 wt.-%, more preferably in the range of 1.0-25 wt.-%, and even more preferably in the range of 1-20 wt.-%, based on the total weight of the microemulsion.

The microemulsion of the present invention further comprises at least one co-surfactant (vi) selected from the group consisting of non-ionic surfactants, mono alcohols, polyols and mixtures thereof. In a preferred embodiment, at least one cosurfactant is selected from the group consisting of monoalcohols, polyols and mixtures thereof. The co-surfactant is different from the non-ionic surfactants of component (iv), from the oily component (ii) and from the polarity modifier (v).

The co-surfactant accumulates—as the surfactants of component (iv)—at the interface between oily component and aqueous phase. By using at least one further co-surfactant the interface layer is packed more densely and is thus more water-repelling, which reduces the possibility of molecular aggregates at the interface.

Suitable co-surfactants may be selected from the group consisting of polyglycerol ester with fatty acids, polyoxyalkylated alkylether, diol, monohydric alcohols, polyoxyalkylated (hydrogenated) oil, and mixtures thereof, but are not limited thereto.

In an even more preferred embodiment, the co-surfactant is selected from the group consisting of diethylene glycol monoethyl ether (DME), polyglycerol-6-dioleate, ethanol, n-propanol, 1,2-propyleneglycol, and polyoxyethylene hydrogenated castor oil, but is not limited thereto.

More preferably, the cosurfactant is selected from the group consisting of DME, ethanol, and 1,2-propylene glycol, in particular of DME and ethanol, and mixtures thereof.

Most preferably, the cosurfactant is ethanol.

In a preferred embodiment the co-surfactant is free of fatty acid mono- or/and diglycerides.

The microemulsion preferably contains 1, 2 or 3 cosurfactants, most preferably one cosurfactant.

The amount of co-surfactant may range from 0.05 to 15 wt.-%, preferably from 0.05 to 10 wt.-% and even more preferably from 0.05 to 5 wt.-%.

The supramolecular aggregation of the amphiphilic substance in the aqueous phase (iii) is a phenomenon caused by the so-called "hydrophobic interactions". Therein, water molecules structure themselves very tightly around the amphiphilic molecules in order to maximise hydrogen bonding. Above a certain concentration, amphiphilic molecules tend to aggregate and as a consequence of the entropic gain generated by the structured water molecules migrate into the aqueous phase.

The overall polarity characteristics of the solvent are conveniently defined by its overall Hildebrand solubility parameter $\delta_t$, which is the sum of a solubility parameter $\delta_H$, which is associated with hydrogen bonds, $\delta_p$ which is associated with polarity interactions, and $\delta_d$ which is associated with v.d. Waals interactions ($\delta_t = \delta_H + \delta_p + \delta_d$).

In case of water as the solvent, $\delta_H$ ($\delta_{H,H2O}$=42.9 $(J/cm^3)^{1/2}$) makes up the bigger part of the overall Hildebrand solubility parameter $\delta_t$ ($\delta_{t,H2O}$=47.9 $J/cm^3)^{1/2}$). Thus, the hydrogen bonds in water cause the high probability of hydrophobic interactions, and thus supramolecular aggregation of the amphiphilic substances.

Consequently, if the probability of supramolecular aggregation of amphiphilic molecules present in the aqueous phase shall be reduced, it is necessary to add agents to the aqueous phase, which are capable of reducing the overall solubility parameter $\delta_t$ and in particular $\delta_H$ of the aqueous phase.

Therefore, at least one polarity modifier (component (v)) is present in the microemulsion according to the invention, which is capable of lowering the overall Hildebrand solubility parameter $\delta_t$ of the aqueous phase.

The polarity modifier can be any substance which is soluble in the aqueous phase and has an overall Hildebrand solubility parameter $\delta_t$ lower than that of water, i.e. lower than 47.9 $(J/cm^3)^{1/2}$ at 25° C. In a preferred embodiment, the polarity modifier has a hydrogen-bond-associated solubility parameter $\delta_H$ which is lower than that of water, i.e. lower than 42.9 $(J/cm^3)^{1/2}$.

Examples for suitable polarity modifiers according to the present invention are ethylacetate ($\delta_t$=18.2 $(J/cm^3)^{1/2}$), 1,3-propyleneglycol ($\delta_t$=28.6 $(J/cm^3)^{1/2}$), methanol ($\delta_t$=29.7 $(J/cm^3)^{1/2}$, $\delta_H$=22.3 $(J/cm^3)^{1/2}$), ethanol ($\delta_t$=26.2 $(J/cm^3)^{1/2}$, $\delta_H$=18.5 $(J/cm^3)^{1/2}$), acetic acid ($\delta_t$=26.4 $(J/cm^3)^{1/2}$, $\delta_H$=18.9 $(J/cm^3)^{1/2}$), isopropanol and glycerol triacetate ($\delta_t$=38.9 $(J/cm^3)^{1/2}$, $\delta_H$=8.9 $(J/cm^3)^{1/2}$), but are not limited thereto.

In a preferred embodiment, the polarity modifier is selected from the group consisting of glycerol triacetate (triacetin), isopropanol, ethanol and 1,3-propyleneglycol and mixtures thereof, most preferably the polarity modifier is glycerol triacetate.

However, in this context it should be noted that the polarity modifier not only inhibits the supramolecular aggregation of the amphiphilic substance, but also prevents the potential supramolecular aggregation of the surfactants/cosurfactants themselves; this is of preferable relevance, as it has been shown by different research groups that HSR side effects can be generated also from the excipients.

The microemulsion preferably comprises 1, 2, 3 or 4 polarity modifiers, most preferably the microemulsion contains one polarity modifier.

The polarity modifier (component (v)) may be present in an amount of 0.1 to 10%, more preferably of 0.1 to 5%, even more preferably of 0.1 to 4 wt.-% based on the total weight of the microemulsion.

In general, a substance can have two different roles due to its physico-chemical properties but according to the present invention, all of the required components in the formulations should be present; e.g. ethanol, which can be both a co-surfactant and a polarity modifier cannot be used alone at the same time as co-surfactant and polarity modifier but as co-surfactant or polarity modifier in the presence of another substance covering the other role.

In a preferred embodiment, the microemulsion according to the invention comprises as amphiphilic substance (component (i)) a pharmaceutically active agent, in particular Docetaxel, as oily component (component (ii)) at least one fatty acid ester of monohydric alcohol, in particular ethyl oleate, as aqueous phase (component (iii)) a pharmaceutically acceptable water, as at least two structurally different non-ionic surfactants (component (iv)) polyoxyalkylene sorbitane fatty acid ethers, in particular polyoxyethylene sorbitane monooleate (Tween 80®) and polyoxyethylene sorbitane laurate (Tween 20®), as polarity modifier (component (v)) triacetin and a co-surfactant (component (vi)), in particular ethanol.

In another preferred embodiment, the microemulsion according to the invention comprises as amphiphilic substance (component (i)) docetaxel, paclitaxel, oxaliplatin or cyclosporin, in particular docetaxel, preferably in an amount of 0.1-2 wt.-%, more preferably 0.2-1.2 wt.-%, based on the total weight of the microemulsion;

as oily component (component (ii)) at least one vegetable oil or/and fatty acid esters of monohydric alcohol, preferably at least one fatty acid ester of monohydric alcohols, preferably a fatty acid ester of ethanol, n-propanol, isopropanol, more preferably a fatty acid ester of ethanol, preferably in an amount of 2-12 wt-%, more preferably of 3-10 wt.-%, based on the total weight of the microemulsion; as aqueous phase (component (iii)) a pharmaceutically acceptable water, preferably a pharmaceutically acceptable water containing citric acid as formulation aid, preferably in an amount of 65-90 wt.-%, more preferably of 70-85 wt.-%, based on the total weight of the microemulsion. as at least two structurally different non-ionic surfactants (component (iv)) polyoxyalkylene sorbitane fatty acid esters and/or polyoxyethylene polyoxypropylene block copolymers, more preferably, polyoxyalkylated sorbitane fatty acid esters, preferably in an amount of 6-16 wt.-%, more preferably in an amount of 7-15 wt.-%, based on the total amount of the microemulsion. as polarity modifier (component (v)) triacetin, ethanol or 1,3-propyleneglycol, more preferably triacetin, preferably in an amount of 0.7-4.2 wt.-%, preferably of 0.9-3.8 wt.-%, based on the total weight of the microemulsion; and as cosurfactant (component (vi)) ethanol, polyglycerol-6-dioleate, DME or mixtures thereof, preferably ethanol, preferably in an amount of 0.5-8.0 wt.-%, more preferably in an amount of 0.7-7 wt.-% based on the total weight of the microemulsion.

as at least two structurally different non-ionic surfactants (component (iv)) polyoxyalkylene sorbitane fatty acid esters and/or polyoxyethylene polyoxypropylene block copolymers, more preferably, polyoxyalkylated sorbitane fatty acid esters, preferably in an amount of 6-16 wt.-%, more preferably in an amount of 7-15 wt.-%, based on the total amount of the microemulsion.

as polarity modifier (component (v)) triacetin, ethanol or 1,3-propyleneglycol, more preferably triacetin, preferably in an amount of 0.7-4.2 wt.-%, preferably in an amount of 0.9-3.8 wt.-%, based on the total weight of the microemulsion; and as cosurfactant (component (vi)) ethanol, polyglycerol-6-dioleate, DME or mixtures thereof, preferably ethanol, preferably in an amount of 0.5-8.0 wt.-%, more preferably in an amount of 0.7-7 wt.-% based on the total weight of the microemulsion.

In a preferred embodiment, the weight ratio of component (iii) to component (ii) is lower than 50:1, more preferably lower than 10:1. and even more preferably between 2:1 and 5:1.

Thus, in a preferred embodiment, the microemulsion according to the present invention is an oil-in-water microemulsion which means that individual droplets of the oily component are distributed within the continuous aqueous phase.

In a preferred embodiment, the mean average diameter of the oily component droplets is in the range of 5 to 10,000 nm, preferably in the range of 10 to 2,000 nm, more preferably in the range of 50 to 1,000 nm. The diameter also includes the non-ionic surfactants assembling at the interface oily component/aqueous phase.

In another embodiment, the weight ratio of component (iii) to component (v) is between 1000:1 to 10:1, preferably 400:1 to 10:1, more preferably between 400:1 to 20:1.

In a further embodiment, the weight ratio of component (iv) to component (vi) may be in the range of 100:1 to 1:1, and more preferably in the range of 10:1 to 2:1.

In the microemulsion according to the present invention, the formation of superaggregates is substantially lowered compared to microemulsions lacking a polarity modifier.

The term "super-aggregate" as used herein means a plurality (at least two) molecules which form larger unities by physical interactions. Therein, the individual molecules are no longer present independently.

Super-aggregation can be measured by dynamic laser light scattering (DLLS) or by UV spectroscopy experiments.

Further, the microemulsions according to the invention are stable, i.e. the droplet size remains unchanged and no superaggregates are formed over time, preferably over a period of 6 months, more preferably over a period of 8 weeks at standard temperature and standard pressure conditions.

The microemulsion, and in particular the pharmaceutical microemulsion, according to the invention are ideally suitable for administration to a patient, in particular for intravenous administration since they can be diluted in any ratios with solutions for infusion, e.g. sterile water, NaCl solution, glucose solution, etc. without any changes in the microemulsion stability and without any superaggregation of both amphiphilic substances and surfactants/co-surfactants being observed.

Thus, the microemulsions according to the present invention are preferably used for reducing or inhibiting the formation of superaggregates in injectables.

Thus, the microemulsions, the pharmaceutical microemulsions, and the injectables made therefrom preferably totally inhibit or largely decrease the HSR (High Sensitivity Reaction) severe side effects.

In vivo experiments evidentiate that i.v. single bolus administration of the microemulsion of the invention does not generate side effects in the animals and lead to good plasma levels of the drug, whereas the i.v. administration of comparative formulations cause severe side effects leading to death of the animals.

Another aspect of the present invention is a process for the manufacture of a microemulsion according to the present invention. Therefore, a mixture of components (i), (ii), (iv), (v) and (vi) is prepared. To the obtained mixture the aqueous phase (component (iii)) is added in several portions under stirring. Finally, the mixture is agitated for another 0.5-3 h.

In another embodiment, the at least one water soluble polarity modifier (v) is dissolved in the aqueous phase (iii) and the resulting solution is added to a mixture of components (i), (ii), (iv) and (vi).

In a preferred embodiment only little energy input is sufficient in order to obtain the stable microemulsion according to the invention. Preferably, it is sufficient to agitate the mixture e.g. with a magnetic stirrer, a paddle stirrer or by hand shaking. Alternatively an homogenizer or an high energy homogenizer can be used.

METHODS

Figure 1:
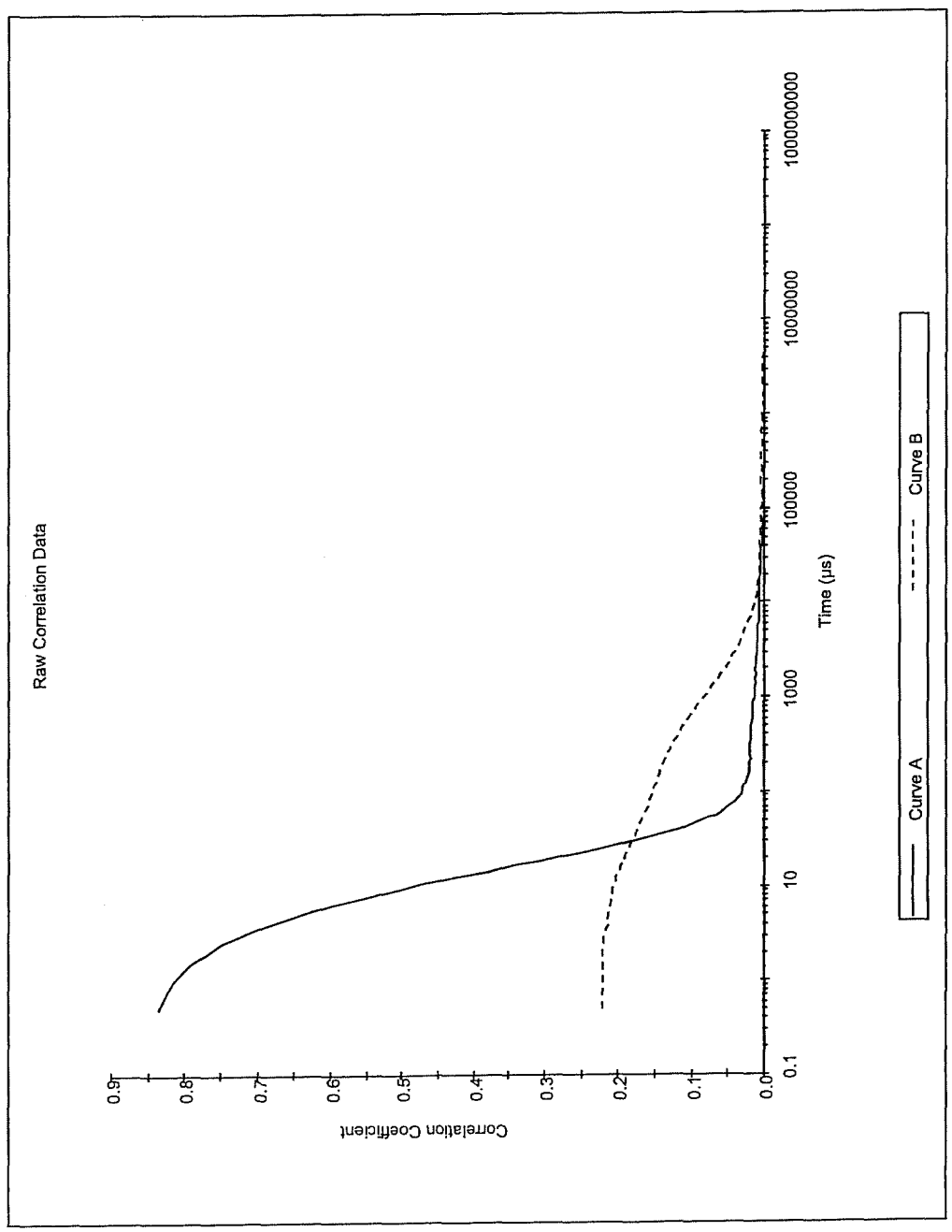
FIG. 1 is a DLLS analysis (correlation coefficient function) of a Tween 80 solution (4 mg/ml) in water (curve A) and a Tween 80 solution (4 mg/ml) in water plus 35 mg/ml triacetin (curve B).

Dynamic Laser Light Scattering (DLLS) was carried out on a Zetasizer Nano S from Malvern Instruments. DLLS is used for measuring the size of the microemulsion oil droplets or size of the supramolecular aggregates (% distribution function modality). Further characterization of supramolecular aggregation is given by the correlation coefficient function modality analysis of the Dynamic Laser Light Scattering.

Blood levels in the pharmacokinetics studies in rats are measured from acetonitrile-extracted plasma samples by HPLC (Agilent 1100 series, UV detector, Zorbax Agilent column Eclipse Plus C-14, water-acetonitrile-methanol-ammonium acetate isocratic method).

Drug assay analysis in stored formulations (stability studies) is carried out by HPLC (Agilent series 1100, UV detector, Zorbax Agilent column Eclipse Plus C-18, water-acetonitrile gradient method).

EXAMPLES

Example 1

250 mg of docetaxel have been added under magnetic stirring for 8 hours to an oily component containing 2.20 g of ethyl oleate, 0.22 g of triacetin, 2.20 g of Tween 80, 1.10 g of Tween 20 and 0.27 g of ethanol.

18.8 g of water for injectables have been added gradually to the oily component containing docetaxel. The microemulsion obtained has been mixed for 1 hour at room temperature.

The weight ratio between the inner oily component and the external aqueous phase is equal to 1:3.0.

The final concentration of docetaxel in the microemulsion is 10 mg/ml.

The quantitative composition (%) of the resulting microemulsion is reported below:

| Composition of Example 1 (wt-%) | |
|---|---|
| DOCETAXEL (i) | 1.00% |
| ETHYL OLEATE (ii) | 8.80% |
| TRIACETIN (iii) | 0.91% |
| TWEEN 80 (iv) | 8.80% |
| TWEEN 20 (v) | 4.40% |
| ETHANOL (vi) | 1.09% |
| WATER (vii) | 75.00% |

Comparative Example 2

200 mg of docetaxel have been added under magnetic stirring at room temperature for 24 hours to an oily component containing 2.48 g of ethyl oleate, 2.48 g of Tween 80, 1.22 g of Tween 20.

18.62 g of water for injectables have been added slowly to the oily component containing docetaxel. The microemulsion obtained has been mixed for 1 hour at room temperature.

The weight ratio between the inner oily component and the external aqueous phase is equal to 1:2.9.

The quantitative composition (%) of the resulting microemulsion is reported below:

| Composition of Comparative Example 2 (wt-%) | |
|---|---|
| DOCETAXEL (i) | 0.80% |
| ETHYL OLEATE (ii) | 9.90% |
| TWEEN 80 (iv) | 9.90% |
| TWEEN 20 (iv) | 4.90% |
| WATER (iii) | 74.50% |

Example 3

0.99 g of docetaxel have been added under magnetic stirring for 8 hours to a mixture containing 19.00 g of ethyl oleate, 18.90 g of Tween 80, 9.48 g of Tween 20 and 1.52 g of ethanol.

148.2 g of water for injectables containing 1.86 g of triacetin and 0.08 g of citric acid have been added gradually to the oily component containing docetaxel. The microemulsion obtained has been mixed for 6 hours at room temperature.

The quantitative composition (%) of the resulting microemulsion is reported below:

| Composition of Example 3 (wt-%) | |
|---|---|
| DOCETAXEL (i) | 0.50% |
| ETHYL OLEATE (ii) | 9.48% |
| TRIACETIN (v) | 0.93% |
| TWEEN 80 (iv) | 9.46% |
| TWEEN 20 (iv) | 4.74% |
| ETHANOL (vi) | 0.76% |
| CITRIC ACID | 0.04% |
| WATER (iii) | 74.10% |

Example 4

108 mg of docetaxel have been added under magnetic stirring for 8 hours to a mixture containing 2.00 g of ethyl oleate, 1.99 g of Tween 80, 0.99 g of Tween 20 and 0.27 g of ethanol.

31.89 g of water for injectables containing 0.40 g of triacetin have been added gradually to the oily component containing docetaxel. The microemulsion obtained has been mixed for 6 hours at room temperature.

The quantitative composition (%) of the resulting microemulsion is reported below:

| Composition of Example 4 (wt-%) | |
|---|---|
| DOCETAXEL (i) | 0.29% |
| ETHYL OLEATE (ii) | 5.32% |
| TRIACETIN (v) | 1.07% |
| TWEEN 80 (iv) | 5.28% |
| TWEEN 20 (iv) | 2.63% |
| ETHANOL (vi) | 0.72% |
| CITRIC ACID | 0.05% |
| WATER (iii) | 84.64% |

Example 5

250 mg of docetaxel have been added under magnetic stirring at room temperature for 8 hours to an oily component containing 0.96 g of ethyl oleate, 0.95 g of triacetin, 1.25 g of Plurol Oleique, 1.27 g of Tween 80 and 0.64 g of Tween 20 and 0.64 g of ethanol.

19.04 g of sterile water for injections have been added slowly to the oily component containing docetaxel. The microemulsion obtained has been mixed for 1 hour at room temperature. The weight ratio between the inner oily component and the external aqueous phase is equal to 1:3.2.

The quantitative composition (%) is reported below:

| Composition of Example 5 (wt-%) | |
|---|---|
| DOCETAXEL (i) | 1.00% |
| ETHYL OLEATE (ii) | 3.84% |
| TRIACETIN (v) | 3.80% |
| PLUROL OLEIQUE (vi) | 5.00% |
| ETOH (vi) | 2.56% |
| TWEEN 80 (iv) | 5.08% |
| TWEEN 20 (iv) | 2.56% |
| WATER (iii) | 76.16% |

Example 6

300 mg of paclitaxel have been dissolved under magnetic stirring at room temperature for 24 hours in an oily mixture containing 4.98 g of Miglyol 812, 1.10 g of Propyleneglycol, 2.00 g of Brij 35, 3.00 g of Pluronic L44 NF and 1.48 g of Cremophor EL.

37.13 g of sterile water for injections have been added slowly to the oily mixture containing paclitaxel. The system is mixed using a paddle mixer at the rate of 270 rpm for 1 hour.

The microemulsion obtained has a concentration of paclitaxel equal to 6 mg/ml.

The weight rate between the oily component and the aqueous phase is 1:2.9.

The quantitative (%) composition is described below:

| Composition of Example 6 (wt-%) | |
|---|---|
| PACLITAXEL (i) | 0.60% |
| MIGLYOL 812 (ii) | 9.96% |
| BRIJ 35 (iv) | 4.00% |
| PLURONIC L44 NF (iv) | 6.00% |
| CREMOPHOR EL (vi) | 2.96% |
| PROPYLENEGLYCOL (v) | 2.21% |
| WATER (iii) | 74.27% |

Example 7

125 mg of oxaliplatin have been added under magnetic stirring at room temperature for 8 hours to 1.31 g of DME. Subsequently 1.34 g of ethyl oleate, 1.31 g soya oil, 1.80 g Pluronic F68, 0.50 g of Triacetin and 1.07 g of Tween 20 have been added to the solution of oxaliplatin in DME.

17.54 g of sterile water for injections have been added gradually to the oily component containing oxaliplatin. The system is mixed using a paddle mixer at the rate of 200 rpm for 1 hour.

The microemulsion obtained has a concentration of oxaliplatin equal to 5 mg/ml.

The weight ratio between the inner oily component and the external aqueous phase is 1:2.4.

The quantitative (%) composition is described below:

| Composition of Example 7 (wt-%) | |
|---|---|
| OXALIPLATIN (i) | 0.50% |
| ETHYL OLEATE (ii) | 5.36% |
| SOYA OIL (ii) | 5.24% |

-continued

| Composition of Example 7 (wt-%) | |
|---|---|
| TWEEN 20 (iv) | 4.28% |
| PLURONIC F68 (iv) | 7.20% |
| DME (vi) | 5.24% |
| TRIACETIN (v) | 2.00% |
| WATER (iii) | 70.18% |

Example 8

200 mg of cyclosporin have been added under magnetic stirring at room temperature for 8 hours to an oily component containing 1.00 g of olive oil, 1.00 g of Akoline MCM, 1.20 g of Tween 80, 0.66 g of Solutol HS 15, 0.44 g of isopropanol and 0.40 g of Ethanol.

15.10 g of sterile water for injections have been added gradually to the oily component containing cyclosporin. The system is mixed using a paddle mixer at the rate of 200 rpm for 1 hour.

The microemulsion obtained has a concentration of cyclosporin equal to 10 mg/ml.

The weight ratio between the oily component and the aqueous phase is 1:3.2.

The quantitative (%) composition is described below:

| Composition of Example 8 (wt-%) | |
|---|---|
| CYCLOSPORIN (i) | 1.00% |
| OLIVE OIL (ii) | 5.00% |
| AKOLINE MCM (ii) | 5.00% |
| TWEEN 80 (iv) | 6.00% |
| SOLUTOL HS 15 (iv) | 3.30% |
| ISOPROPANOL (v) | 2.20% |
| ETOH (vi) | 2.00% |
| WATER (iii) | 75.50% |

Example 9

200 mg of docetaxel have been added under magnetic stirring for 6 hours to a mixture containing 15.9 g of ethyl oleate, 15.9 g of Tween 80, 7.9 g of Tween 20 and 0.28 g of ethanol.

157.5 g of water for injectables containing 2 g of Triacetin and 0.32 g of citric acid have been gradually added to the oily mixture containing docetaxel. The microemulsion obtained has been mixed for 7 hours at room temperature.

The quantitative composition (%) of the resulting microemulsion is reported below:

| Composition of Example 9 (wt-%) | |
|---|---|
| DOCETAXEL (i) | 0.20% |
| ETHYL OLEATE (ii) | 7.95% |
| TRIACETIN (v) | 1.00% |
| TWEEN 80 (iv) | 7.94% |
| TWEEN 20 (iv) | 3.97% |
| ETHANOL (vi) | 0.14% |
| CITRIC ACID | 0.06% |
| WATER (iii) | 78.74% |

In order to monitor the level of molecular aggregation in solution, Dynamic Laser Light Scattering (DLLS) has been used. Using this technique, it is not necessary to dilute the sample.

FIG. 1 shows the DLLS analysis of a solution of the non-ionic surfactant Tween 80 (curve A) at a concentration of 4 mg/ml, i.e. above the CMC (critical micellar concentration) of the surfactant. A regular symmetric correlation function is registered, showing a symmetric size distribution of colloidal molecular aggregates originated by the micelles of the surfactant. The addition of triacetin to the aqueous solution (curve B) prevents the formation of the surfactant micelles.

Figure 2:
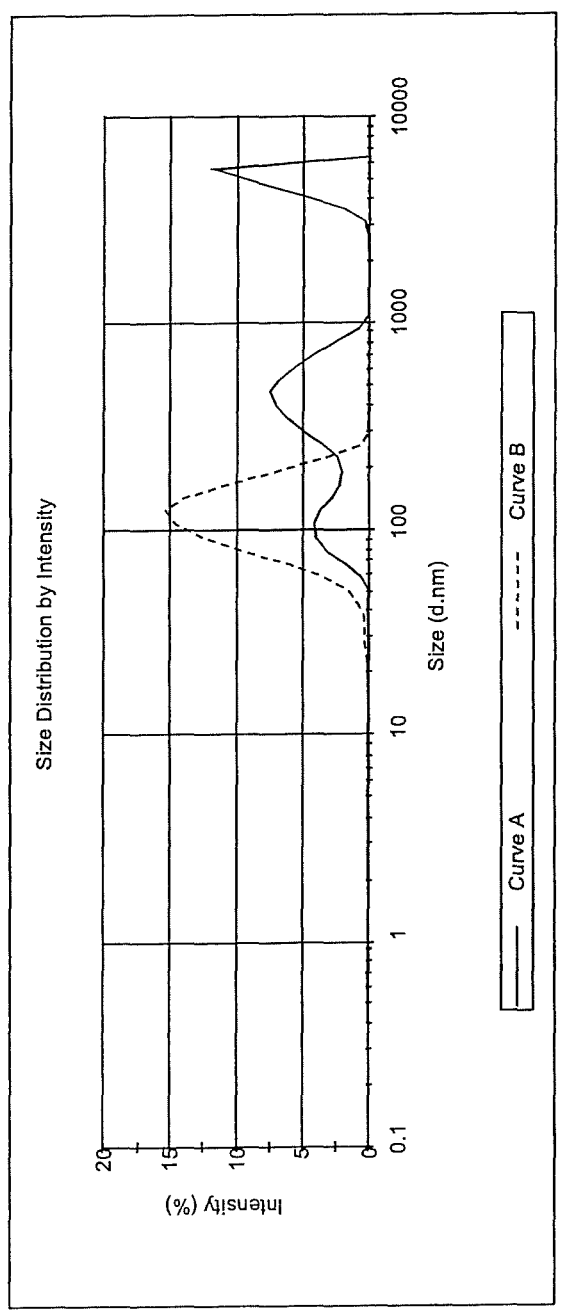
FIG. 2 is a DLLS analysis (% volume distribution function) of tetracycline solution (20 μg/ml) in water (curve A) and tetracycline solution (20 μg/ml) plus 30 mg/ml glycerol in water (curve B).

FIG. 2 shows the DLLS analysis (size volume % distribution function) of the amphiphilic drug tetracycline in water. Curve A (tetracycline (20 µg/ml) in water) evidentiates 3 peaks corresponding to aggregates of 3 different sizes (80 nm, 600 nm, 5000 nm), curve B shows that the addition of glycerol (30 mg/ml) eliminates the larger aggregates; at a higher concentration of glycerol (90 mg/ml) no aggregates are observed.

Figure 3:
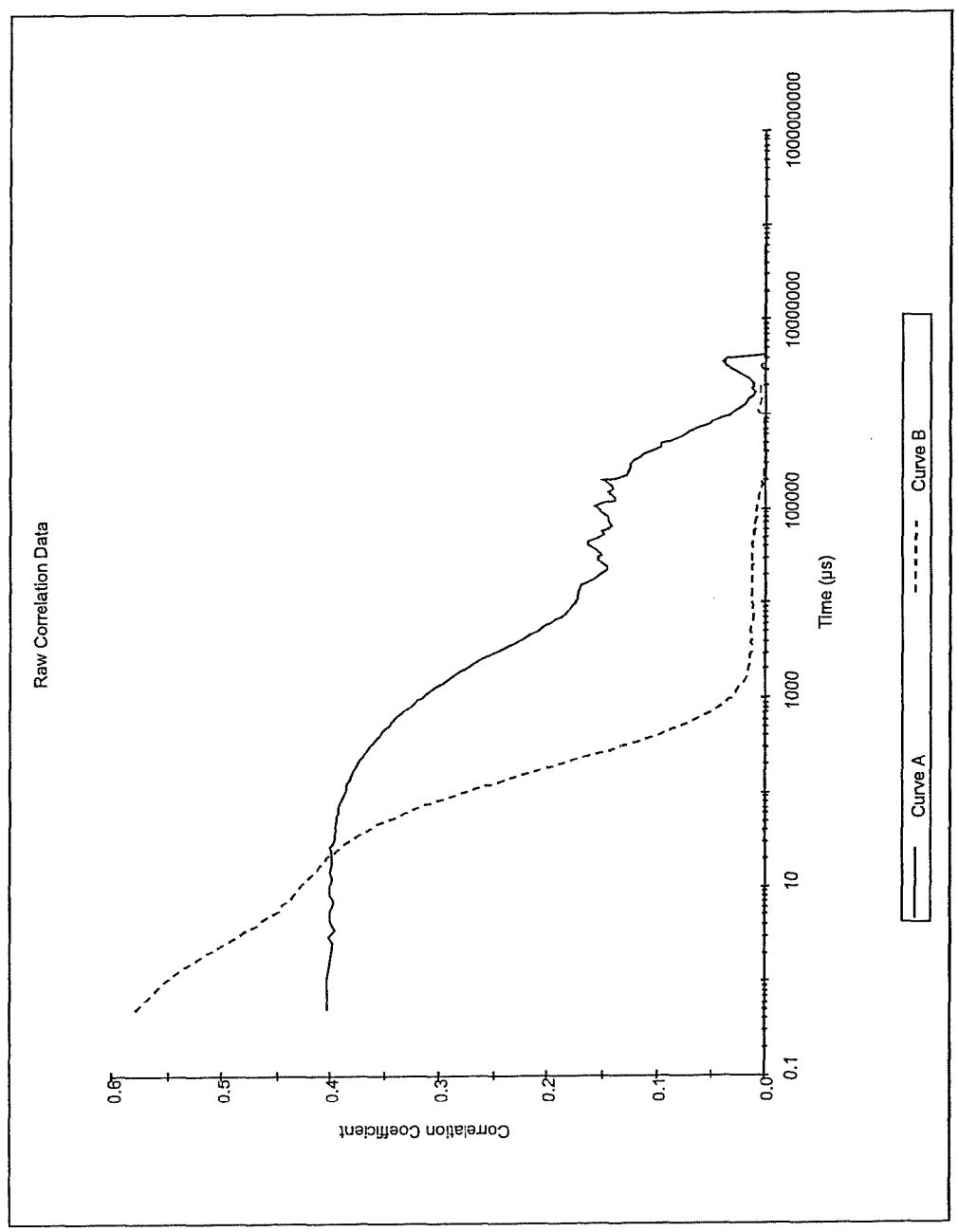
FIG. 3 is a DLLS analysis (correlation coefficient function) of an aqueous docetaxel solution (curve A) and an as described solution containing additionally 10 mg/ml triacetin (curve B).

FIG. 3 shows the DLLS analysis (correlation coefficient function) of the amphiphilic drug docetaxel (50 µg/ml) in water. Curve A (docetaxel in water) evidentiates the presence of aggregates; addition of triacetin (10 mg/ml) (curve B) greatly reduces supramolecular aggregation whereas addition of 30 mg/ml of triacetin totally eliminates the presence of molecular aggregates.

Figure 4:
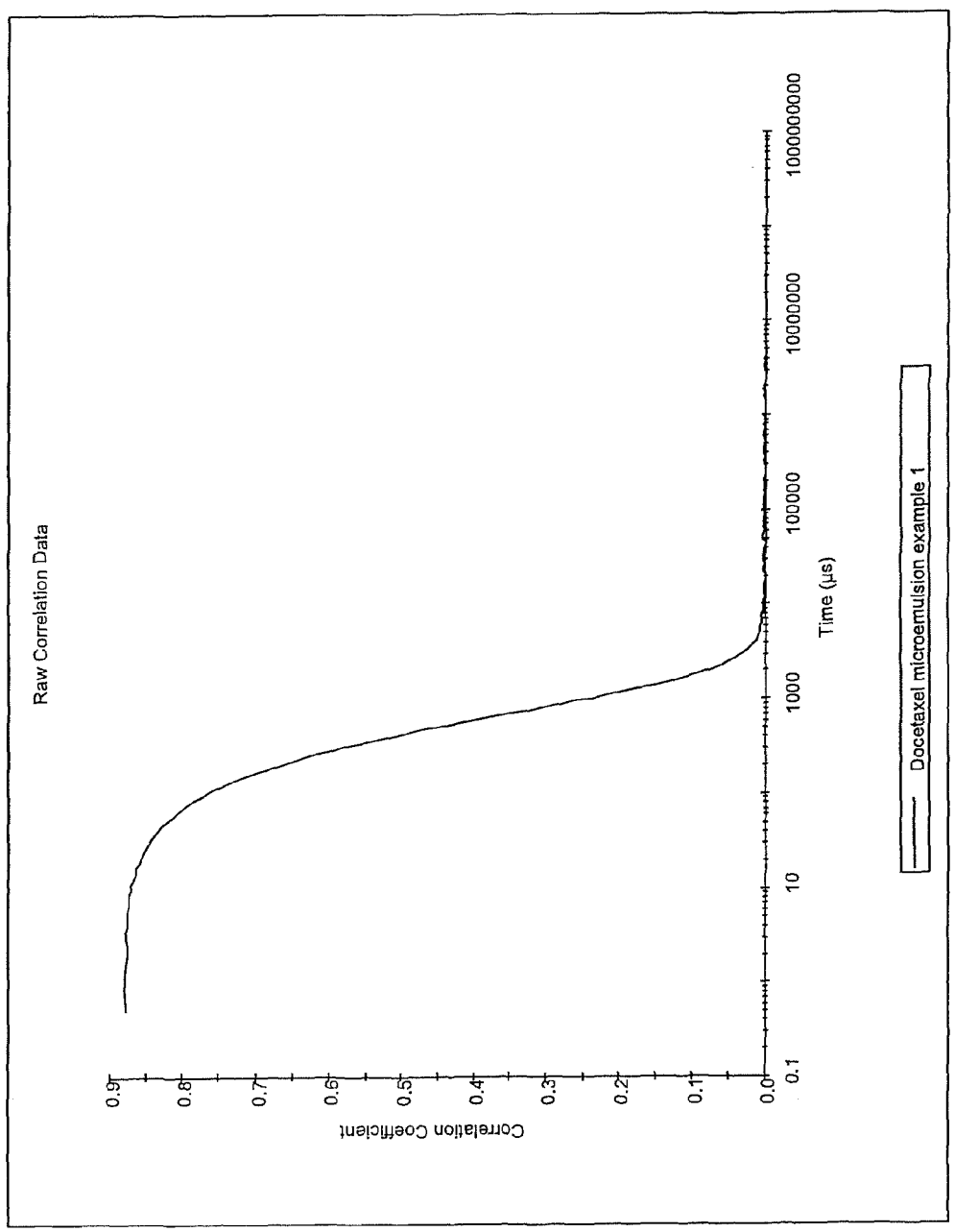
FIG. 4 shows a DLLS analysis (correlation coefficient function) of the docetaxel containing microemulsion of Example 1.
Figure 5:
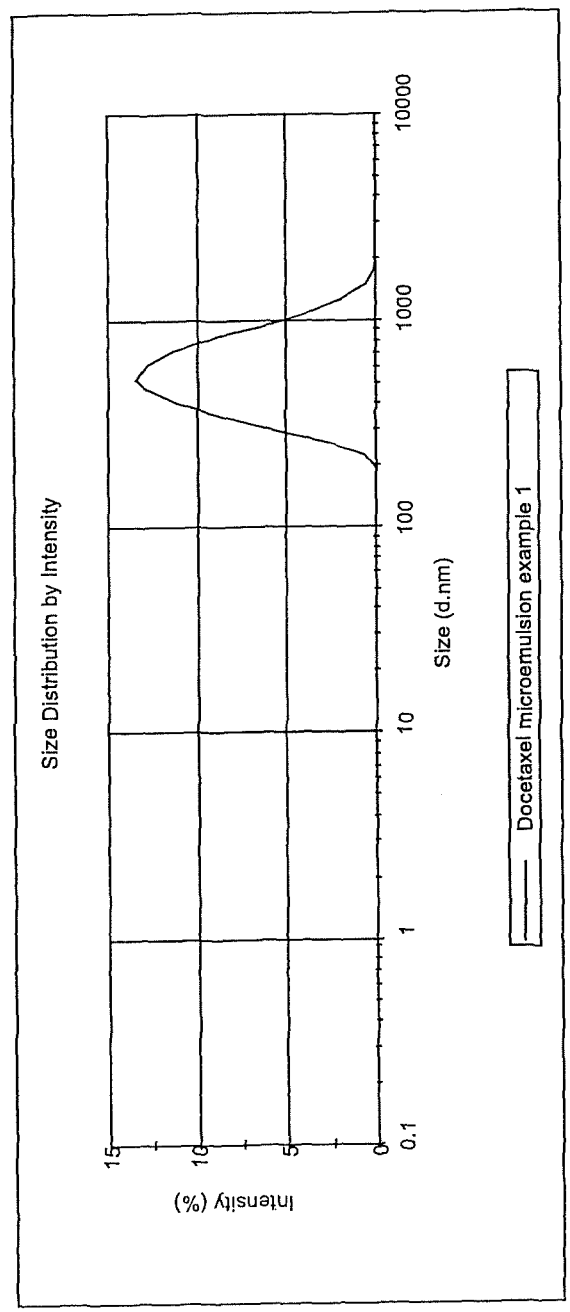
FIG. 5 shows a DLLS analysis (% intensity distribution function) of the docetaxel containing microemulsion of Example 1.

DLLS analysis of the docetaxel microemulsion of example 1 is reported in FIGS. 4 and 5: the correlation coefficient function (FIG. 4) evidentiates the presence of only one regular symmetrical scattering distribution function corresponding to the monomodal size distribution of the microemulsion droplets (FIG. 5). No supramolecular aggregates are detected.

Figure 6:
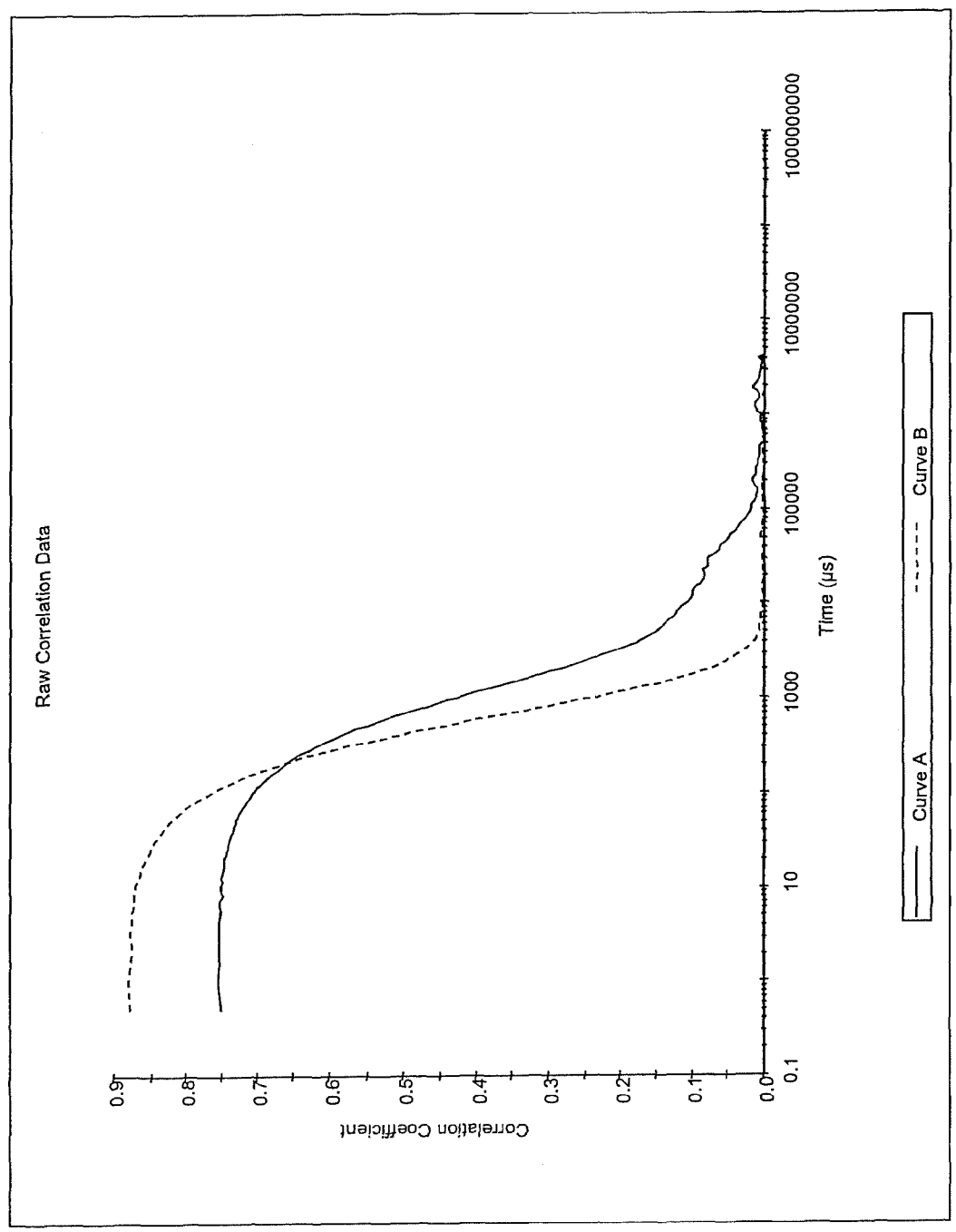
FIG. 6 shows a DLLS analysis (correlation coefficient function) of the microemulsion of Comparative Example 2 (curve A) and of Example 1 (curve B).

DLLS (correlation coefficient function) analysis of the docetaxel microemulsion of Comparative Example 2 (curve A) is reported in FIG. 6 compared with the data of the microemulsion of Example 1 (curve B) as a reference: the correlation coefficient function curve A evidentiates the deviation from a regular symmetrical scattering distribution function, showing the coexistence of aggregates/precipitates and oil droplets of the microemulsion.

These results clearly demonstrate the role of the polarity modifier triacetin and cosurfactant ethanol, the only components present in the microemulsion of Example 1 but not in the one of Comparative Example 2.

Figure 7:
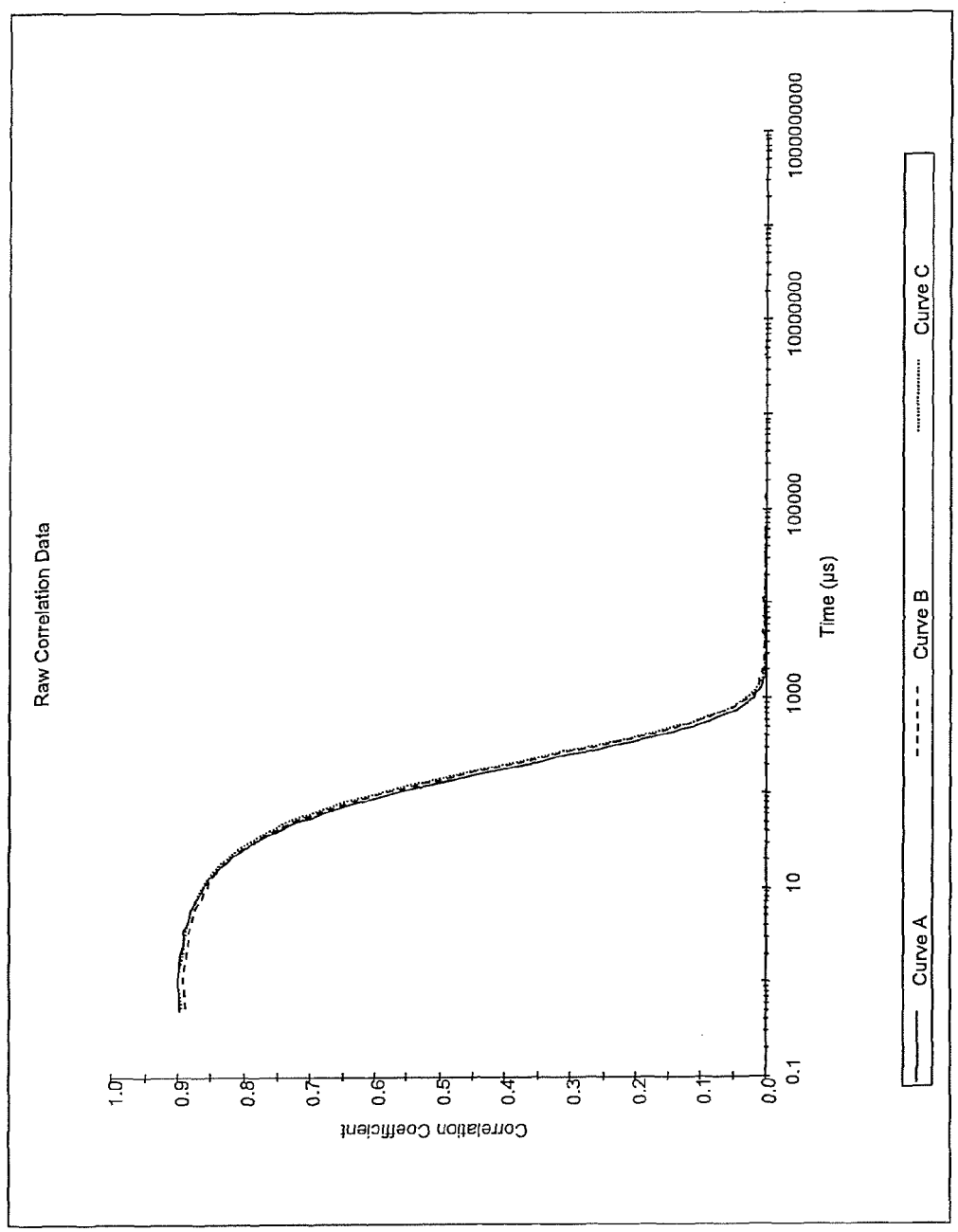
FIG. 7 shows a DLLS analysis (correlation coefficient function) of the microemulsion of Example 1 at different times (curve A (t=0), curve B (t=1 hour), curve C (t=4 hours)) after dilution with 0.9% NaCl.
Figure 8:
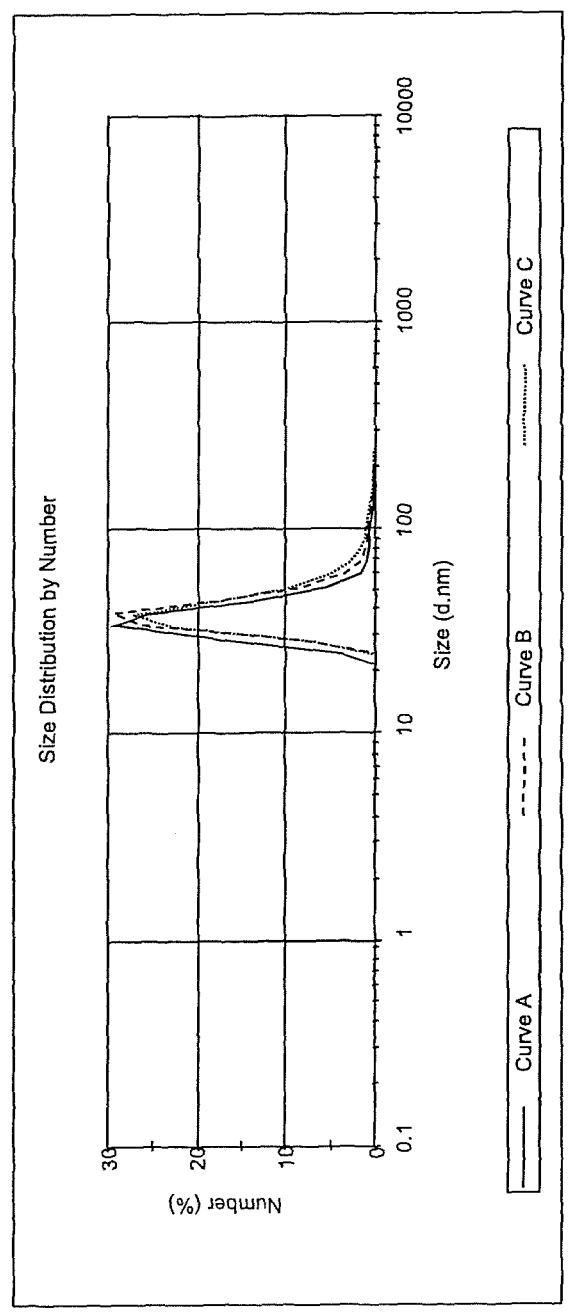
FIG. 8 shows a DLLS analysis (% number distribution function) of the docetaxel containing microemulsions of Example 1 diluted with infusion physiological solution 0.9% NaCl (curve A. (t=0); curve B (t=1 hour); curve C (t=4 hours).

The DLLS analysis of the Docetaxel microemulsion of Example 1 after dilution (1/20) with infusion physiological solution 0.9% NaCl at different times is reported in FIGS. 7 and 8: the correlation coefficient function (FIG. 7) evidentiates the presence of only one regular symmetrical scattering distribution function at all times which corresponds to the monomodal size distribution of the microemulsion droplets (FIG. 8) and shows the absence of any supramolecular aggregates or precipitate.

Figure 9:
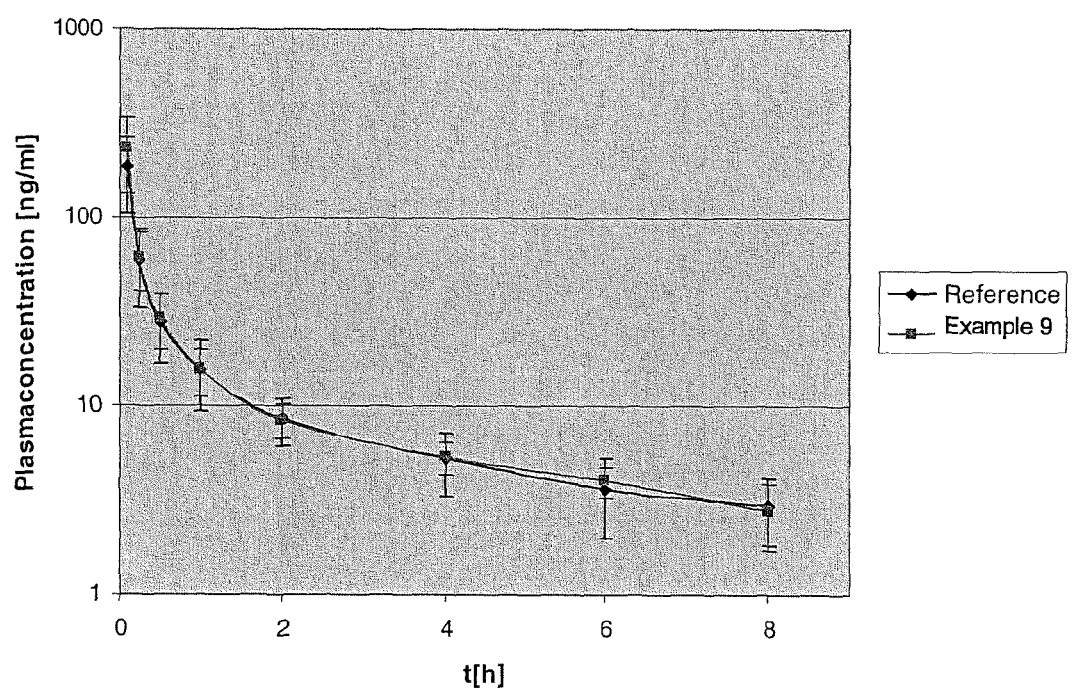
FIG. 9 shows the mean (medium) plasma concentration time curves of Docetaxel after administration of the microemulsions according to Example 9 and TAXOTERE® (Reference).

FIG. 9 shows the mean (medium) plasma concentration time curves of Docetaxel after administration of the microemulsions according to Example 9 and TAXOTERE® (Reference).

A pharmacokinetic study (single bolus injection) on a rat animal model has been carried out investigating the microemulsion of Example 1. The data were compared with the formulation TAXOTERE® already on the market. The experimental procedure which has been followed is reported below:
a) Sprague Dawley (Harlan Italy) rats, weight range 0.4-0.5 kg; 6 animals are used for each formulation;
b) rat tail vein and arteria are incanulated with a catheter for both bolus dose administration (vein) and blood sampling (arteria);
c) single bolus docetaxel dose of 10 mg/kg body is administered over 30 second into catheter;
d) blood samples are collected at time 5', 10', 15', 30', and 60';
e) plasma is separated by centrifugation in heparinezed vials;
f) docetaxel is extracted by acetonitrile and dried under vacuum;
g) docetaxel content in the dried sample is determined by HPLC;
h) HPLC was an AGILENT series 1100, with an UV detector, column Agilent Zorbax Eclipse XDB-C18.

In Table 1 the AUC derived from plasma levels is reported.

TABLE 1

Pharmacokinetic Studies in Sprague Dawley Rats

| | TAXOTERE ® | MICROEMULSION EXAMPLE 1 |
|---|---|---|
| AUC[1] | 394.95 ± 24.61 µg/ml/min | 340.47 ± 26.43 µg/ml/min |

[1]AUC is derived from experimental plasma docetaxel concentrations at all blood sampling times; docetaxel concentration at t = 0 is calculated by mathematical function extrapolation from all other data.
The values of AUC of the microemulsion of the invention are not statistically different (at $p = 0.05$ and $p = 0.01$) from the AUC of TAXOTERE ®.

Further, another pharmacokinetic study in rats has been carried with the microemulsion of Comparative Example 2. The experimental procedure which has been followed is reported below:
a) Spague Dawley rats (3), weight range 0.4-0.5 kg;
b) rat tail vein and arteria are incanulated with a catheter for both bolus dose administration (vein) and blood sampling (arteria);
c) single bolus docetaxel dose of 10 mg/kg body is administered over 30 second into catheter;

Animals show shortly after beginning of administration severe HSR-related side effects, i.e. pain, breath difficulties, trembling and die within a few minutes (3 subjects out of 3).

A further pharmacokinetic study (continuous perfusion) on a rat animal model has been carried out investigating the microemulsion of Example 3. The data were compared with the formulation TAXOTERE® already on the market. The experimental procedure which has been followed is reported below:
a) Sprague Dawley (Harlan Italy) rats, weight range 0.4-0.5 Kg; 6 animals are used for each formulation;
b) rat tail vein and arteria are incanulated with a catheter for dose administration (vein) and blood sampling (arteria); to the vein catheter a peristaltic pump is connected;
c) docetaxel dose of 20 mg/kg body is administered over 180 minutes by continuous perfusion into the vein catheter (perfusion rate of 5 ml/60 min);
d) blood samples are collected at time 20', 40', 60', 90', 120 and 180';
e) plasma is separated by centrifugation in heparinezed vials;
f) docetaxel is extracted by acetonitrile and dried under vacuum;
g) docetaxel content in the dried sample is determined by HPLC;
h) HPLC was an AGILENT series 1100, with an UV detector, column Agilent Zorbax Eclipse XDB-C18.

In Table 2 the docetaxel plasma concentrations generated by the perfusion study are reported.

TABLE 2

Docetaxel perfusion study in Sprague Dawley rats

| Time (min) | Docetaxel plasma concentration (µg/ml) | |
|---|---|---|
| | Taxotere ® | Microemulsion Example 3 |
| 20 | 4.20 ± 0.75 | 3.72 ± 1.83 |
| 40 | 4.87 ± 1.19 | 4.77 ± 2.06 |
| 60 | 3.98 ± 1.54 | 5.05 ± 1.45 |
| 90 | 0.57 ± 0.08 | 1.03 ± 0.39 |
| 120 | 0.33 ± 0.09 | 0.59 ± 0.19 |
| 180 | 0.16 ± 0.18 | 0.32 ± 0.10 |

From the data reported in Table 2 it is concluded that the microemulsion of example 3 is generating plasma docetaxel levels comparable to those of the marketed formulation Taxotere®.

In table 3 the stability data of the docetaxel microemulsion formulation of example 4 are shown; the docetaxel concentrations (analyzed by HPLC as reported in the Methods paragraph) remain stable for the storage period.

TABLE 3

Docetaxel stability at R.T. in microemulsion of example 4

| Time (months) | Docetaxel concentration (mg/g) |
|---|---|
| 0 | 29.8 |
| 1 | 29.7 |
| 3 | 29.4 |
| 6 | 29.7 |

A further pharmacokinetic study (single bolus injection) on a beagle dog animal model has been carried out investigating the microemulsion of Example 9. The data were compared with those obtained with the formulation TAXOTERE® already on the market. The experimental procedure which has been followed is reported below.
  (a) beagle dogs (Halan, Germany), twelve animals are used for each formulation;
  (b) cross-over design;
  (c) intravenous infusion;
  (d) formulations are diluted with physiological solution (NaCl 0.9%);
  (e) single bolus Docetaxel dose of 0.6 mg/kg body weight is administered over one hour;
  (f) plasma samples are collected at five minutes, 10 minutes, 15 minutes, 30 minutes, 60 minutes, 1 hour, 2 hours, 4 hours, 6 hours, 8 hours;
  (g) plasma is separated by centrifugation in heparinized vials;
  (h) Docetaxel is extracted by acetonitrile and dried under vacuum;
  (i) Docetaxel content in the dried sample is determined by HPLC;
  (j) HPLC was an AGILENT series 1100 with an UV detector, column AGILENT ZORBAX ELLIPSE XDB-C18.

As can be seen from the pharmacokinetic study in FIG. 9, the plasma concentration after administration of the microemulsion according to Example 9 over time in beagle dogs is almost identical to the plasma concentration after having administered TAXOTERE® (Example 9). (See FIG. 9). The values of AUC of the microemulsion of the invention are statistically equivalent compared to the AUC of TAXOTERE® (121.56 ng/ml/h for the microemulsion of example 9 vs. 111.97 ng/ml/h for TAXOTERE®; (CV=30%).

REFERENCES

1. TAXOL® (paclitaxel) Injection (Bristol-Myers Squibb)—Prescribing Information
2. TAXOTERE® (docetaxel) Injection Concentrate (Sanofi Aventis)—Prescribing Information
3. Sharma A. et al., Cancer Res., 53, 5877, 1993
4. Essayan D. et al., J. Allergy Clin. Immunol., 97, 42, 1996
5. Mertens W. et al., Annals of Oncology, 5, 185, 1994
6. Tyson L. et al., Abstract N. 2260, ASCO Annual Meeting, 1999
7. Alberts D. and Gareia D., Drugs, 4, 30, 1997
8. Szebeni J, Crit. Rev. Ther. Drug Carrier Syst., 15, 57, 1998
9. Wong-Beringer A. et al., Clin. Infect. Dis., 27, 603, 1998
10. Costa S. et al., Current Opinion in Critical Care, 7, 379, 2001
11. Lavasanipar A. et al., Pharm. Res., 19, 418, 2002
12. Gaboriav F. et al., Antimicrobial Agents and Chemotherapy
13. Sanchez-Brunete J. et al., J. Drug Targeting, 12, 453, 2004
14. Szebeni J. et al., Intern. Immunopharmacology, 1, 721, 2001
15. Gelman K., Lancet, 344, 1267, 1994
16. Cortesj. et al., J Clin. Oncol., 13, 2643, 1995
17. Denman J. et al., J. Clin. Oncol., 20, 2760, 2002
18. Sharma et al., J. Pharm. Sci., 84, 1400, 1995
19. Szebeni J. and Alving C., WO 1999/022759

The subject-matter of the following items is also comprised by the present invention.
1. Microemulsion comprising
  (i) at least one amphiphilic substance,
  (ii) at least one oily component,
  (iii) an aqueous phase,
  (iv) at least two structurally different non-ionic surfactants, and
  (v) at least one polarity modifier and
  (vi) at least one cosurfactant.
2. Microemulsion according to item 1, wherein the amphiphilic substance is an amphiphilic pharmaceutically active agent.
3. Microemulsion according to any of items 1 or 2, wherein the solubility of the amphiphilic substance is less than 5 g/l in water, preferably less than 0.5 g/l.
4. Microemulsion according to any one of items 1-3, wherein the amphiphilic pharmaceutically active agent is selected from the group consisting of taxanes or taxane derivatives such as paclitaxel, docetaxel, etoposide, vinblastine, doxorubicin, epirubicin, idarubicine; platinum compounds such as cisplatin, carboplatin, oxaliplatin; cyclosporin, ansamycin, erythromycin, tetracycline, amphotericin B, enalapril, salbutanol, zometabine and droperidol.
5. Microemulsion according to any of items 1 to 4, wherein the amphiphilic pharmaceutically active agent is a taxane or a taxane derivative.
6. Microemulsion according to any one of items 1-5, wherein component (i) is present in an amount of 0.0001 to 5.0 wt.-% based on the total weight of the microemulsion.
7. Microemulsion according to any one of items 1 to 6, wherein the oily component (ii) is selected from the group consisting of fatty acids and fatty acid esters.

8. Microemulsion according to any one of items 1-7, wherein the oily component (ii) is present in an amount of 0.1 to 25 wt.-% based on the total weight of the microemulsion.
9. Microemulsion according to any of items 1-8, wherein the aqueous phase (iii) comprises water and optionally water soluble formulation aids.
10. Microemulsion according to any of items 1-9, wherein the aqueous phase (iii) is present in an amount of 40 to 95 wt.-% based on the total weight of the microemulsion.
11. Microemulsion according to any one of items 1-10, wherein the non-ionic surfactants (iv) are selected from the group consisting of alkylglucosides, polyoxyalkylene alkyl ethers, polyoxyalkylene alkyl phenols, polyoxyalkylene fatty acid esters, polyoxyalkylene glycerol fatty acid esters, polyoxyalkylene sorbitane fatty acid esters, polyoxyalkylene block-copolymers, polyglycerol fatty acid esters, polyoxyalkylene glycerides, polyoxyalkylene sterols, polyoxyalkylene vegetable oils, polyoxyalkylene hydrogenated vegetable oils, polyglycerol ether, polyoxyalkylene glycerol ester, and polyvinylalcohol.
12. Microemulsion according to any one of items 1-11, wherein component (iv) is present in an amount of 0.1 to 25 wt.-% based on the total weight of the microemulsion.
13. Microemulsion according to any one of items 1-12, wherein the polarity modifier (component (v)) has an overall solubility parameter $\delta_t$ of lower than 47.9 $(J/cm^3)^{1/2}$.
14. Microemulsion according to any of items 1-13, wherein the polarity modifier has an hydrogen bond associated solubility parameter $\delta_H$ of lower than 42.9 $(J/cm^3)^{1/2}$.
15. Microemulsion according to any one of items 1-14, wherein the polarity modifier is soluble in water.
16. Microemulsion according to any one of items 1-16, wherein the polarity modifier is selected from the group consisting of ethylacetate, propylene-glycol, methanol, ethanol, acetic acid and glycerol triacetate, and is preferably glycerol triacetate.
17. Microemulsion according to any one of items 1-16, wherein the polarity modifier is present in an amount of 0.1 to 10 wt.-% based on the total weight of the microemulsion.
18. Microemulsion according to any one of items 1-17, wherein the co-surfactant (vi) is selected from the group consisting of non-ionic surfactants, mono alcohols, polyols and mixtures thereof.
19. Microemulsion according to any one of items 1-18, wherein the cosurfactant (vi) is present in an amount of 0.05 to 15 wt.-% based on the total weight of the microemulsion.
20. Microemulsion according to any one of items 1-19 wherein the weight ratio of component (iii) to component (ii) is lower than 50:1.
21. Microemulsion according to any one of items 1-20, wherein the weight ratio of component (iii) to component (v) is 1000:1 to 10:1.
22. Microemulsion according to any one of items 1-21, wherein the microemulsion is an oil-in-water microemulsion.
23. Microemulsion according to any of items 1-22, wherein the formation of superaggregates is reduced compared to microemulsions lacking a polarity modifier or/and a cosurfactant.
24. Microemulsion according to any of items 1-23, wherein the mean average diameter of the oil droplets is in the range of 5 to 10,000 nm.
25. Microemulsion according to any of items 1-24 comprising
    as amphiphilic substance a pharmaceutically active agent,
    as oily component at least one fatty acid ester of monohydric alcohols,
    as aqueous phase a pharmaceutically-acceptable water,
    as at least two structurally different non-ionic surfactants polyoxyalkylene sorbitane fatty acid esters,
    as polarity modifier triacetin; and
    a co-surfactant.
26. Microemulsion according to any of items 1-24, comprising
    as amphiphilic substance (component (i)), docetaxel, paclitaxel, oxaliplatin or cyclosporin,
    as oily component (component (ii)) at least one fatty acid ester of monohydric alcohols,
    as aqueous phase (component (iii)) a pharmaceutically acceptable water,
    as at least two structurally different non-ionic surfactants (component (iv)) polyoxyalkylene sorbitane fatty acid esters,
    as polarity modifier (component (v)) triacetin and
    as cosurfactant (component (vi)) ethanol and/or DME.
27. Microemulsion according to item 26, wherein
    the amphiphilic substance is Docetaxel,
    the oily component is ethyl oleate,
    the at least two structurally different non-ionic surfactants are polyoxyethylene sorbitane monooleate (Tween 80®) and polyoxyethylene sorbitane monolaurate (Tween 20®) and the co-surfactant is ethanol.
28. Process of manufacturing a microemulsion according to any of items 1 to 25, comprising the steps of
    (a) preparing a mixture of components (i), (ii), (iv), (v) and (vi),
    (b) adding component (iii) to the mixture obtained in a) under stirring in several portions and
    (c) further agitating the mixture obtained in b).
29. Use of the microemulsion according to items 1-25 for the manufacture of a pharmaceutical composition for administration to a patient.
30. Use according to item 27, wherein the pharmaceutical composition is an injectable formulation.
31. Use according to item 28 for reducing or inhibiting the formation of superaggregates in injectables.

The invention claimed is:
1. A microemulsion comprising
   (i) an amphiphilic pharmaceutically active agent in an amount of 0.1 to 2 wt %,
   (ii) at least one oily component in an amount of 3 to 10 wt %,
   (iii) an aqueous phase in an amount of 65 to 90 wt %,
   (iv) at least two structurally different non-ionic surfactants in an amount of 6-16 wt %,
   (v) at least one polarity modifier in an amount of 0.7 to 4.2 wt, wherein at least one of said polarity modifiers is triacetin, and
   (vi) at least one co-surfactant in an amount of 0.5 to 8 wt %, wherein the co-surfactant is selected from ethanol or diethylene glycol monoethyl ether, wherein said at least one co-surfactant is different from the non-ionic surfactants of component (iv), from the oily component (ii) and from the polarity modifier (v).
2. The microemulsion according to claim 1, wherein the amphiphilic pharmaceutically active agent is selected from the group consisting of paclitaxel, docetaxel, etoposide, vinblastine, doxorubicin, epirubicin, and idarubicine.

3. The microemulsion according claim 1, wherein the oily component (ii) is selected from the group consisting of fatty acids and fatty acid esters.

4. The microemulsion according to claim 1, wherein the aqueous phase (iii) comprises water and optionally water soluble formulation aids.

5. The microemulsion according to claim 1, wherein the non-ionic surfactants (iv) are selected from the group consisting of alkylglucosides, polyoxyalkylene alkyl ethers, polyoxyalkylene alkyl phenols, polyoxyalkylene fatty acid esters, polyoxyalkylene glycerol fatty acid esters, polyoxyalkylene sorbitane fatty acid esters, polyoxyalkylene block-copolymers, polyglycerol fatty acid esters, polyoxyalkylene glycerides, polyoxyalkylene sterols, polyoxyalkylene vegetable oils, polyoxyalkylene hydrogenated vegetable oils, polyglycerol ether, polyoxyalkylene glycerol ester, and polyvinylalcohol.

6. The microemulsion according to claim 1, wherein the polarity modifier (component (v)) has an overall solubility parameter $\delta_t$ of lower than 47.9 $(J/cm^3)^{1/2}$, in particular a hydrogen bond associated solubility parameter $\delta_H$ of lower than 42.9 $(J/cm^3)^{1/2}$.

7. The microemulsion according to claim 1, further comprising a second polarity modifier selected from the group consisting of ethylacetate, propyleneglycol, methanol, ethanol, and acetic acid.

8. The microemulsion according to claim 1, wherein the weight ratio of component (iii) to component (ii) is lower than 50:1 and the weight ratio of component (iii) to component (v) is 1000:1 to 10:1.

9. The microemulsion according to claim 1, wherein the formation of super aggregates is reduced compared to microemulsions lacking a polarity modifier or/and a cosurfactant.

10. The microemulsion according to claim 1, which is an oil-in-water microemulsion.

11. The microemulsion according claim 1, wherein
said oily component is at least one fatty acid ester of monohydric alcohols,
said aqueous phase is a pharmaceutically-acceptable water,
said at least two structurally different non-ionic surfactants are polyoxyalkylene sorbitane fatty acid esters, and
said polarity modifier is triacetin.

12. The microemulsion according to claim 1, wherein said amphiphilic substance (component (i)), is docetaxel or paclitaxel,
said oily component (component (ii)) is at least one fatty acid ester of monohydric alcohols,
said aqueous phase (component (iii)) is a pharmaceutically acceptable water,
said at least two structurally different non-ionic surfactants (component (iv)) are polyoxyalkylene sorbitane fatty acid esters,
said polarity modifier (component (v)) is triacetin and
said cosurfactant (component (vi)) is ethanol and/or DME.

13. The microemulsion according to claim 12 wherein
the amphiphilic substance is Docetaxel,
the oily component is ethyl oleate,
the at least two structurally different non-ionic surfactants are polyoxyethylene sorbitane monooleate (Tween 80®) and polyoxyethylene sorbitane monolaurate (Tween 20®) and the co-surfactant is ethanol.

14. A process of manufacturing a microemulsion according to claim 1, comprising the steps of
(a) preparing a mixture of components (i), (ii), (iv), (v) and (vi),
(b) adding component (iii) to the mixture obtained in a) under stirring in several portions and
(c) further agitating the mixture obtained in b).

15. A method for making an injectable formulation comprising combining a microemulsion according to claim 1, with formulation aid suitable for use in an injectable formulation.

16. A pharmaceutical composition comprising
(a) a microemulsion comprising
(i) an amphiphilic substance that is a taxane or a taxane derivative in an amount of 0.1 to 2 wt %,
(ii) at least one oily component in an amount of 3 to 10 wt %,
(iii) an aqueous phase in an amount of 65 to 90 wt %,
(iv) at least two structurally different non-ionic surfactants in an amount of 6-16 wt %,
(v) at least one polarity modifier in an amount of 0.7 to 4.2 wt, wherein at least one of said polarity modifiers is triacetin, and
(vi) at least one co-surfactant in an amount of 0.5 to 8 wt %, wherein the co-surfactant is selected from ethanol or diethylene glycol monoethyl ether,
wherein said at least one co-surfactant is different from the non-ionic surfactants of component (iv), from the oily component (ii) and from the polarity modifier (v), and
(b) a pharmaceutically acceptable water, buffer or solution.

17. The microemulsion according to claim 1, wherein the amphiphilic pharmaceutically active agent is a taxane or taxane derivative.

18. The microemulsion according to claim 10, wherein the mean average diameter of the oil droplets in the continuous aqueous phase is in the range of 5 to 10,000 nm.

* * * * *